(12) United States Patent
Wreyford

(10) Patent No.: US 7,018,845 B2
(45) Date of Patent: Mar. 28, 2006

(54) METHOD FOR STAGED OXIDATION FOR ENHANCED NITROGEN AND SULFUR DETECTION

(75) Inventor: Randy L. Wreyford, Spring, TX (US)

(73) Assignee: Petroleum Analyzer Company, LP, Houston, TX (US)

( * ) Notice: Subject to any disclaimer, the term of this patent is extended or adjusted under 35 U.S.C. 154(b) by 0 days.

(21) Appl. No.: 10/165,634

(22) Filed: Jun. 7, 2002

(65) Prior Publication Data

US 2003/0032194 A1 Feb. 13, 2003

Related U.S. Application Data

(62) Division of application No. 09/264,377, filed on Mar. 5, 1999, now Pat. No. 6,458,328.

(51) Int. Cl.
| | |
|---|---|
| G01N 21/72 | (2006.01) |
| G01N 25/26 | (2006.01) |
| G01N 21/62 | (2006.01) |
| G01N 1/00 | (2006.01) |
| G01N 21/76 | (2006.01) |

(52) U.S. Cl. .................. 436/155; 436/160; 436/43; 436/147; 436/149; 436/152; 436/171; 436/174; 436/172; 422/78; 422/69; 422/80; 422/88; 422/89; 422/82.05; 422/82.07; 422/82.08; 422/82.09; 73/1.01; 73/1.02; 73/23.2; 73/23.31

(58) Field of Classification Search .................. 436/43, 436/147, 149, 152, 165, 155, 174, 160, 171, 436/172; 422/78, 69, 80, 88, 89, 82.05, 82.07, 422/82.08, 82.09; 73/1.01, 1.02, 23.2, 23.31
See application file for complete search history.

(56) References Cited

U.S. PATENT DOCUMENTS

| | | | |
|---|---|---|---|
| 2,431,632 A | | 11/1947 | Brandt .................. 23/284 |
| 3,003,853 A | | 10/1961 | Mccorney et al. ............. 23/207 |
| 3,957,441 A | * | 5/1976 | Baba ........................... 23/259 |
| 3,985,505 A | * | 10/1976 | Bredeweg ................... 436/160 |
| 4,066,409 A | * | 1/1978 | Fine |
| 4,070,155 A | * | 1/1978 | Fraim |
| 4,071,324 A | | 1/1978 | Reid ............................ 23/288 |
| 4,120,663 A | | 10/1978 | Fally .......................... 422/198 |
| 4,282,183 A | * | 8/1981 | Bredeweg et al. ............. 428/78 |
| 4,293,308 A | * | 10/1981 | Sisti et al. |
| 4,352,779 A | * | 10/1982 | Parks |
| 4,352,781 A | * | 10/1982 | O'Brien |
| 4,622,009 A | * | 11/1986 | Bredeweg |
| 4,814,612 A | * | 3/1989 | Vestal et al. |
| 4,843,016 A | * | 6/1989 | Fine |
| 4,914,037 A | * | 4/1990 | Forster et al. ............... 436/106 |
| 4,916,077 A | * | 4/1990 | Forster et al. ............... 436/160 |
| 4,950,456 A | * | 8/1990 | Forster et al. ................. 422/80 |
| 5,028,544 A | * | 7/1991 | Rasulev et al. |
| 5,064,617 A | * | 11/1991 | O'Brien et al. |
| 5,080,577 A | * | 1/1992 | Bell et al. |
| 5,285,071 A | * | 2/1994 | LeCount |
| 6,075,609 A | * | 6/2000 | Tarkanic et al. ............. 356/417 |

* cited by examiner

Primary Examiner—Jill Warden
Assistant Examiner—Brian Sines
(74) Attorney, Agent, or Firm—Robert W. Strozier

(57) ABSTRACT

A more efficient method for combustion or oxidation of samples containing nitrogen, phosphorus and/or sulfur to their corresponding oxides is disclosed, where method uses multi-staged addition of an oxidizing agent to enhance oxidation and liberation of nitrogen, phosphorus and/or sulfur oxides for subsequent detection. The method of the present invention allows for the injection of larger samples or the introduction of a greater amount of sample per unit of time which results in a larger amount of analyte being delivered to the detector per unit of time, thereby improving detection limits and detection efficiency.

56 Claims, 5 Drawing Sheets

METHOD FOR STAGED OXIDATION FOR ENHANCED NITROGEN AND SULFUR DETECTION

RELATING APPLICATIONS

This application is a divisional of U.S. patent application Ser. No. 09/264,377 filed 5 Mar. 1999 now U.S. Pat. No. 6,458,328.

BACKGROUND OF THE INVENTION

1. Field of the Invention

The present invention relates to a staged oxidation chamber where a sample and an oxidizing agent are introduced into a oxidation chamber to form an oxidizing mixture and subsequently at least another portion of oxidizing agent is introduced to the oxidizing mixture to enhance oxidation and the production of nitrogen and/or sulfur oxides for subsequent detection.

More particularly, the present invention relates to a multi-staged combustion chamber where an influent of a sample and excess oxidizing agent are introduced into the chamber maintained at an elevated temperature to form an oxidizing mixture and subsequently at least one additional portion of oxidizing agent is introduced to the oxidizing mixture which results in enhanced oxidation efficiency, enhanced liberation and oxidation of chemically bound nitrogen and/or sulfur and improved detection sensitivity for nitrogen, sulfur, chlorides and/or phosphorus.

2. Description of the Related Art

Many analytical systems require conversion of the chemical components into derived chemical components that are capable of detection in a given detection device. Often the conversion requires partial to complete conversion of the chemical components to their oxides. Generally, this is accomplished by combustion of the chemical components in the presence of an oxygen containing gas. However, when the chemical components to be oxidized include large amount of hydrocarbons and small amount of elemental constituents that are of interest, then oxidation efficiency becomes a significant impediment to detectability and ultimate detection limits and sensitivities.

Thus, oxidation or combustion chambers that improve oxidation or combustion efficiencies represent an advancement in the art especially relating to the detection of small elemental constituents such as nitrogen, phosphorus and/or sulfur where highly efficient oxidation greatly enhances detection reproducibility, sensitivity and detection limits.

SUMMARY OF THE INVENTION

The present invention provides a multi-staged combustion or oxidation device including a combustion tube having a sample introduction line and at least two oxidizing agent introduction lines. The sample introduction line and an inert gas introduction line are associated with a device inlet where the inert gas carries the sample into a first combustion zone where the sample and carrier are mixed with a first amount of oxidizing agent from the first oxidizing agent introduction line to form an oxidizing mixture. The second oxidizing agent introduction line is located a distance d downstream from the first combustion zone and supplies a second amount of oxidizing agent to the mixture in a second combustion zone to enhances combustion of the sample and liberation of nitrogen, phosphorus and/or sulfur oxides. Additional oxidizing agent introduction lines can also be included in the device.

The present invention provides a multi-staged combustion or oxidation device including a combustion tube having a sample introduction line and at least two oxidizing agent introduction lines. The sample introduction line and one of the oxidizing agent introduction lines are associated with a device inlet and the second oxidizing agent introduction line is located a distance d downstream from the inlet which establishes two combustion zones. Additional oxidizing agent introduction lines can also be included in the device.

The present invention provides a multi-staged combustion or oxidation device including a combustion tube having a sample introduction line and at least two oxidizing agent introduction lines. The sample introduction line and one of the oxidizing agent introduction lines are associated with an interface operably connected to a device inlet and the second oxidizing agent introduction line is located a distance d downstream from the inlet which establishes two combustion zones. Additional oxidizing agent introduction lines can also be included in the device.

The present invention also provides nitrogen, phosphorus and/or sulfur detection systems with improved sensitivity, detection limits and reproducibility incorporating one of the above-described combustion devices.

The present invention further provides detection systems including an oxidation device of the present invention designed for direct injection or optionally coupled to a separation device by an interface and a post oxidation device transformation device coupled to a detection system.

The present invention also provides methods for enhanced detection of nitrogen, phosphorus and/or sulfur present in a sample where the method incorporates sample oxidation in a multi-staged combustion device of the present invention.

DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1:
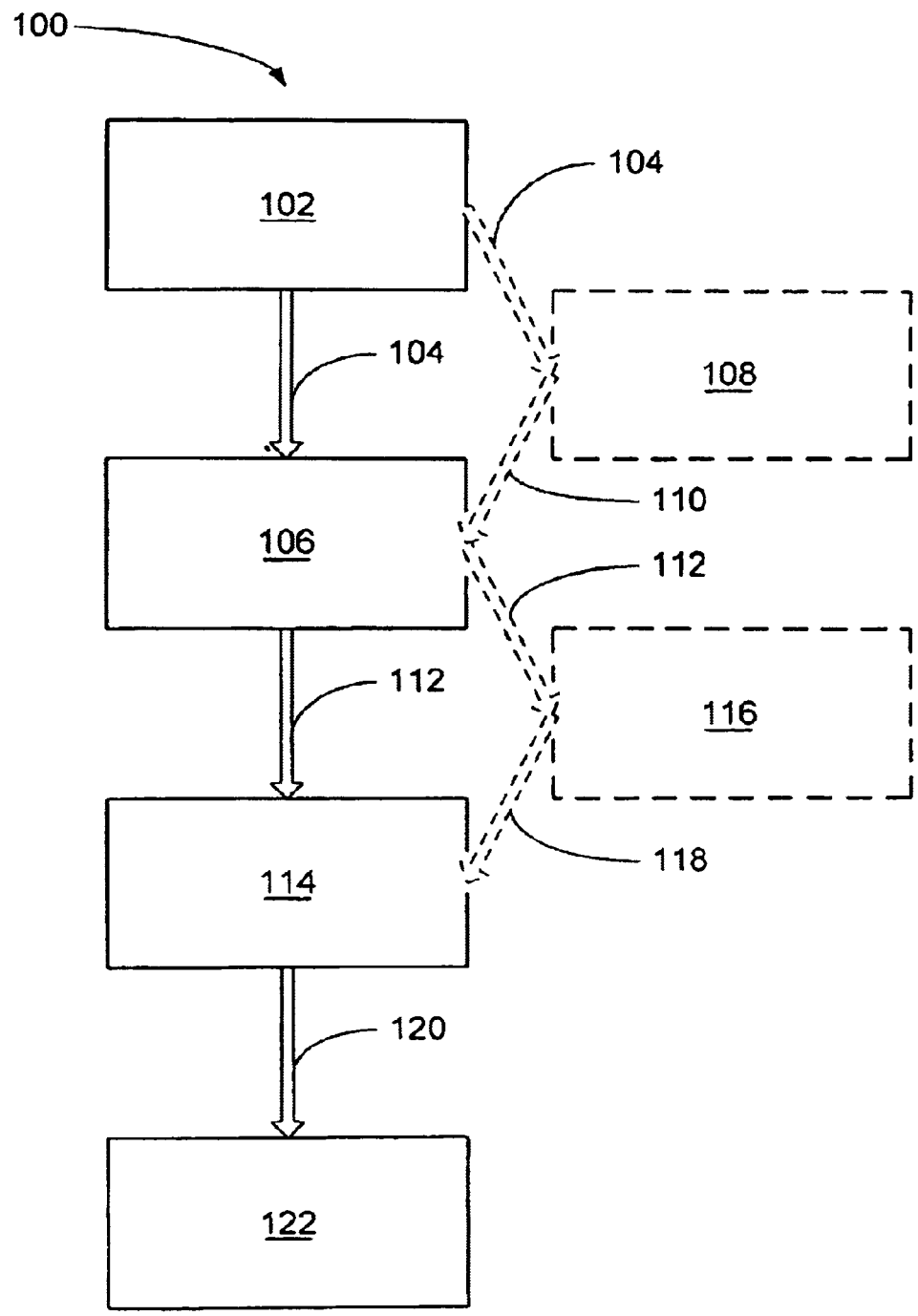
FIG. 1 is a block diagram of an analytical system 100 of the present invention shown generally to include separation device 102, combustion device 106, optional interface 108, detector 114, optional transformation device 116 and analyzer 122.

The inventor has found that a more efficient combustion or oxidation device can be designed for the formation of nitrogen, phosphorus and/or sulfur oxides from a sample containing these elemental constituents. The device uses multi-staged addition of an oxidizing agent to enhance oxidation and liberation of nitrogen, phosphorus and/or sulfur oxides for subsequent detection by nitrogen, phosphorus and/or sulfur specific detectors. The oxidation devices of the present invention allow for the injection of larger samples or the introduction of a greater amount of sample per unit of time which results in a larger amount of analyte being delivered to the detector improving detection limits and detection efficiency. The devices may be utilized for gas, liquid and solid samples. For example the devices of the present invention allows for a sample injection of from about 1 μL to 200 μL at about 0.5 μL/sec to about 6 μL/sec, more preferably for a sample injection of from about 60 μL to about 100 μL at about 3 μL/sec to about 5 μL/sec.

Broadly, the present invention discloses a multi-staged combustion device including a sample inlet which can be a septum for direct injection or a sample delivery system operably connected thereto and at least two oxidizing agent introduction lines operably connected to an oxidizing agent delivery system. The device also includes an oxidation or combustion tube, where the sample is oxidized by the oxidizing agent, and an outlet through which the oxidized sample exits the device.

Generally, a first amount of oxidizing agent is introduced in an amount sufficient to convert a portion of the oxidizable components in the sample into their corresponding oxides. Preferably, the first introduction of oxidizing agent is in excess of an amount sufficient to oxidize all oxidizable components in the sample into their corresponding oxides. The sample and the first amount of oxidizing agent mix to form an oxidizing mixture (a mixture actively undergoing oxidation) which occurs in a first combustion region or zone of the combustion tube. The combustion tube being maintained at an elevated temperature generally between about 300° C. and about 1600° C. Preferably, the flow rate of the first amount of oxidizing agent is generally between about 50 cc/min and about 1000 cc/min and more preferably between about 200 cc/min and about 400 cc/min.

At a point downstream of the first combustion zone, the device includes a second oxidizing agent introduction inlet, line or port where a second amount of oxidizing agent is introduced into the oxidizing mixture. The second amount of oxidizing agent has a given flow rate and direction of introduction. This second amount of oxidizing agent acts to improve oxidation efficiency and to enhance the formation of nitrogen, phosphorus and/or sulfur oxides for subsequent species specific detection. The second amount of oxidizing agent is thought to result in enhanced oxidation and liberation of chemically bound nitrogen, phosphorus and/or sulfur through enhanced mixing and the disruption of flow related channeling, i.e., an increase in turbulent mixing and thus oxidation.

The second introduction of oxidizing agent occurs downstream from the first combustion zone. Preferably, the second inlet is located at least 1 cm and preferably at least 5 cm from the sample inlet. And particularly, the second inlet is located at or near a mid-point of the reaction tube. A preferred tube configuration is a tube within a tube where the first combustion zone is associated with the interior of the inside tube and the second combustion zone is associated with the region between the outer surface of the inner tube and the inner surface of the outer tube. Another preferred tube configuration is that of a U-shaped tube with the second inlet directed into the tube just prior to, at or just after the U turn.

Preferably, the flow rate of the second amount of oxidizing agent is sufficient to cause increased turbulent mixing of the oxidizing mixture and is generally between about 10 cc/min and 300 cc/min, more preferably between about 20 cc/min and about 100 cc/min, and most preferably between about 40 cc/min and about 60 cc/min. Although the introduction direction of the second amount of oxidizing agent into the tube is not critical, the inventor has found that if the flow rate is in a direction different from a direction of flow of the oxidizing mixture, then turbulent mixing appears to be improved.

The device can include additional oxidizing agent introduction inlets, ports or delivery systems to further enhance oxidation efficiencies. However, the inventor has found that a single secondary oxidizing agent inlet is sufficient; provided that the second inlet is a distance d downstream from the sample inlet.

The present invention also relates to analytical systems incorporating the combustion device described above. The systems generally include a separation device that chromatographically separates a sample into its molecular components or molecular profiles. An effluent from the separation device is then forwarded to the combustion device of the present invention. The effluent may also include an oxidizable or non-oxidizable carrier. The effluent is then mixed with oxidizing agent, preferably oxygen gas, at or prior to introduction into the combustion device which is maintained at an elevated temperature to facilitate sample component oxidation.

The analytical systems of the present invention can also include a sample interface interposed between and operatively connected to the separation device and the combustion device where the interface is designed to thoroughly mix the separation effluent and the first amount of oxidizing agent prior to or upon introduction into the combustion device. Generally, the interface is a nebulizer or atomizer adapted to convert the effluent and oxidizing agent into an oxygen rich aerosol. The aerosol is then forwarded to the combustion device.

The analytical systems of the present invention can also include a post-combustion transformation device where specific oxides are converted to other species capable of detection in a species specific detector. Such transformation devices include, without limitation, reduction devices where oxides of sulfur are reduced to sulfur species capable of ozone induced chemiluminescence.

The analytical systems of the present invention are ideally suited to detect nitrogen and/or sulfur in a given sample component where component typically refers to a specific molecular species, but may refer to a set of molecular species that are not fully resolved by the separation device utilized. In such analytical systems, the nitrogen and/or sulfur is generally detected either by UV fluorescence or ozone induced chemiluminescence.

The present invention also relates to methods for efficient oxidation of samples or sample components, to methods of detecting specific elemental constituents of samples or sample components such as nitrogen, phosphorus or sulfur. The oxidization method broadly includes the step of mixing a sample with a first amount of an oxidizing agent to form an oxidizable mixture. The mixture is then forwarded into a combustion tube or zone maintained at an elevated temperature and oxidized. Subsequent to mixture introduction and oxidation commencement, a second amount of oxidizing agent is introduced into the tube or zone to enhance combustion or oxidation efficiency and to enhance the liberation and formation of nitrogen, phosphorus and sulfur oxides from nitrogen, phosphorus and/or sulfur in the sample.

The detection methods of the present invention generally involves separating a sample into components or into a profile of components (peaks containing a multitude of individual molecular species). The sample components or sample profile is then forwarded to a multi-staged combustion device of the present invention. Optionally, the sample effluent can be converted into an aerosol comprising the sample effluent and a first amount of a gaseous oxidizing agent which can then be forwarded to the multi-stage combustion device.

The effluent or optionally the aerosol is introduced into a sample inlet to a combustion zone of the combustion device to form an oxidizing mixture. The combustion zone is maintained at an elevated temperature to facilitate conversion of the combustible sample component to their corresponding oxides. Of course, the effluent can comprise sample components in a combustible or non-combustible carrier or solvent.

Downstream from the inlet, a second amount of the gaseous oxidizing agent is introduced into the combustion tube at a given flow rate. The second introduction can be in any direction relative to a flow of the oxidizing mixture, i.e., 0° to 180°. Preferably, the introduction is in a direction different from the flow of the oxidizing mixture, i.e., an angle greater than 0°, and particularly, the introduction direction should be at an angle between about 30° to 180° relative to the flow direction of the oxidizing mixture.

Alternatively, if the flow of the oxidizing mixture is associated with the structure of the combustion tube, a good approximation, then the second addition direction angle can be relative to the tube structure at the point of introduction.

After undergoing complete or efficient oxidation, the oxidized effluent (which of course also contains water) is forwarded to a detector capable of analyzing for a given oxide such as NO, $NO_2$, $SO_2$, or the like. The detected signal is then electrically forwarded to an analyzing unit that converts the raw detector signal into a spectra or data which relates the signal to a concentration of the sample component being detected at that time. Optionally, the oxidized effluent from the combustion device or oxidation device can be forwarded a chemical transformation device that converts one or more classes of oxides to other molecular species capable of post-transformation detection. Such transformations include reduction of sulfur oxides to sulfur species capable of ozone induced chemiluminescence. The reduction can be carried out in such a way as to reduce the sulfur oxides and maintain a sufficient concentration of nitrogen oxides so that the NO can be directly observed by ozone induced nitrogen chemiluminescence.

The combustion tube used in the present invention can be any tube that can with stand the temperatures generated during combustion and do not adversely interfere with sample oxidation by adsorbing or absorbing components. Preferred tube materials include, without limitations, metals such as stainless steel or other similar non-staining steel alloys, titanium and titanium alloys, quartz, silica or silicates, alumina or aluminates, silica-alumina mixed ceramics and other high temperature ceramics.

Referring now to FIG. 1, an analytical system of the present invention is shown in block diagram generally 100 to include a separation device 102 which can be a GC, LC, MPLC, HPLC, CE (capillary electrophoresis), CEC, GPC (gel permeation chromatography), SEC (size exclusion chromatography), and other separation devices. An effluent 104 from the separation device 102 is then forwarded to a combustion device 106 where the effluent is mixed with an oxidizing agent and converted partially or completely into its corresponding oxides. Optionally, the effluent 104 can be forwarded to an interface 108 where the effluent 104 is combined with the oxidizing agent to form an effluent-agent mixture 110, preferably an atomized mixture and particularly an aerosol.

The effluent 104 or mixture 110 is then forwarded to the combustion device 106. The effluent 104 or the mixture 110 is converted in the combustion device 106 into an oxidized effluent 112 comprising oxides of the components that comprise or make-up the separated sample, effluent or mixture. As stated previously, the combustion device 106 uses at least one additional injection of oxidizing agent into the device 106 to improve oxidation efficiency and improve the formation of nitrogen, phosphorus and sulfur oxides. The oxidized effluent 112 can then be forwarded to a detector 114.

Optionally, oxidized effluent 112 can be forwarded to a transformation device 116 where the oxidized effluent 112 or a constituent of the oxidized effluent are converted to a transformed effluent 118 comprising transformed oxides species capable of post-conversion detection by the detector 114. The detector 114 detects either a specific component of the oxidized effluent 112 or transformed effluent 118 to produce a signal 120 which can be directly stored, printed, archived, plotted, etc. or preferably forwarded electrically, optically, electromagnetically, or the like to an analyzer 122. The analyzer 122 converts the signal 120 which can be continuous (analog) or discreet (digital) into data related to a concentration of the detected signal 120 in the sample, sample component or effluent.

Figure 2:
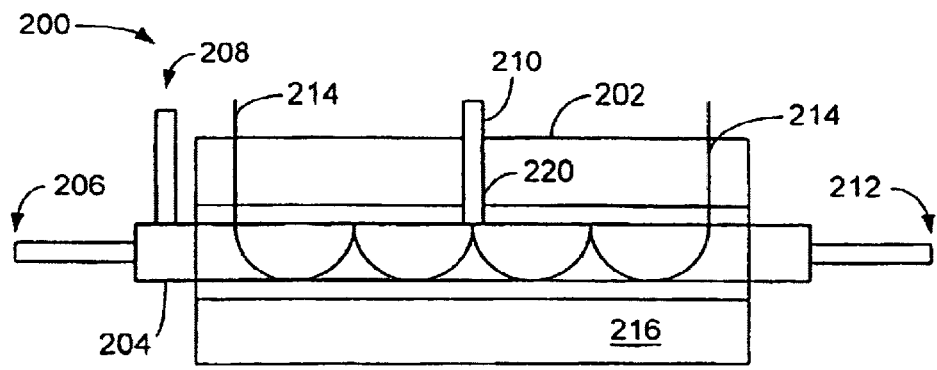
FIG. 2 is a cross-sectional view of an embodiment of a combustion device 200 of the present invention shown generally to include housing 202, combustion tube 204, sample inlet 206, a first oxidizing agent inlet 208, a second oxidizing agent inlet 210 and an outlet 212.

Referring now to FIG. 2, an embodiment of the combustion device generally 200 of the present invention is shown to include a housing 202 enclosing a combustion tube 204 having a sample inlet 206, a first oxidizing agent inlet 208, a second oxidizing agent inlet 210 downstream from the first inlet 208 and an outlet 212. The device 200 also includes a heater 214 and preferably an insulator 216. The combustion tube 204 can be a single tube with a side arm 218 attached thereto at or near a mid-point 220 of the tube 204.

Figure 3:
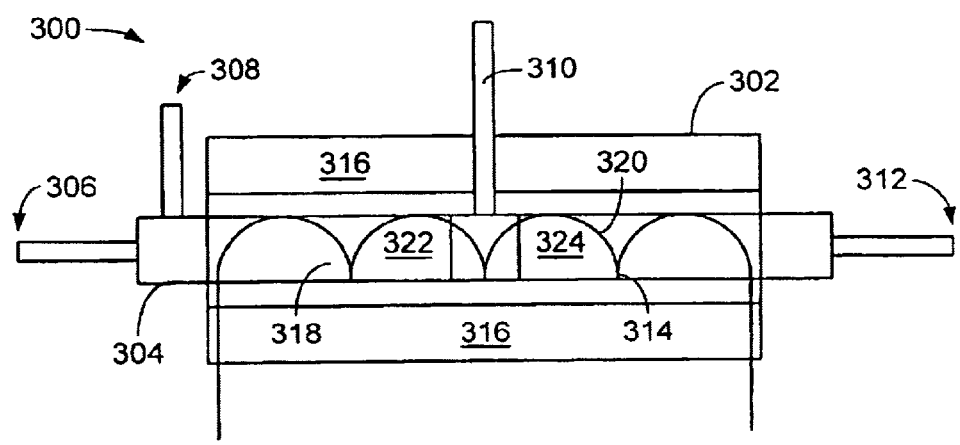
FIG. 3 is a cross-sectional view of an embodiment of a combustion device 300 of the present invention shown generally to include a housing 302 combustion tube 304 having a sample inlet 306, a first oxidizing agent inlet 308, a second oxidizing agent inlet 310 downstream from the first inlet 308, outlet 312, a first tube segment 318 and a second tube segment 320.

Alternatively, as shown in FIG. 3, another embodiment of the combustion device generally 300 of the present invention is shown to include a housing 302 enclosing a combustion tube 304 having a sample inlet 306, a first oxidizing agent inlet 308, a second oxidizing agent inlet 310 downstream from the first inlet 308 and an outlet 312. The device 300 also includes a heater 314 and preferably an insulator 316. The tube 304 can comprise a first tube segment 318 and a second tube segment 320 with the second oxidizing agent inlet 310 interposed therebetween in the form of a T-connection, but other similar connection can be used as well. As the sample and the first amount of oxidizing agent enter the first segment 318, oxidation commences in a first oxidation zone 322. When the oxidizing mixture reaches the second oxidizing agent inlet 310, a second amount of oxidizing agent in injected into the mixture. This second amount of oxidizing agent improves oxidation efficiency in a second oxidizing zone 324 associated with the second tube segment 320.

Figure 4:
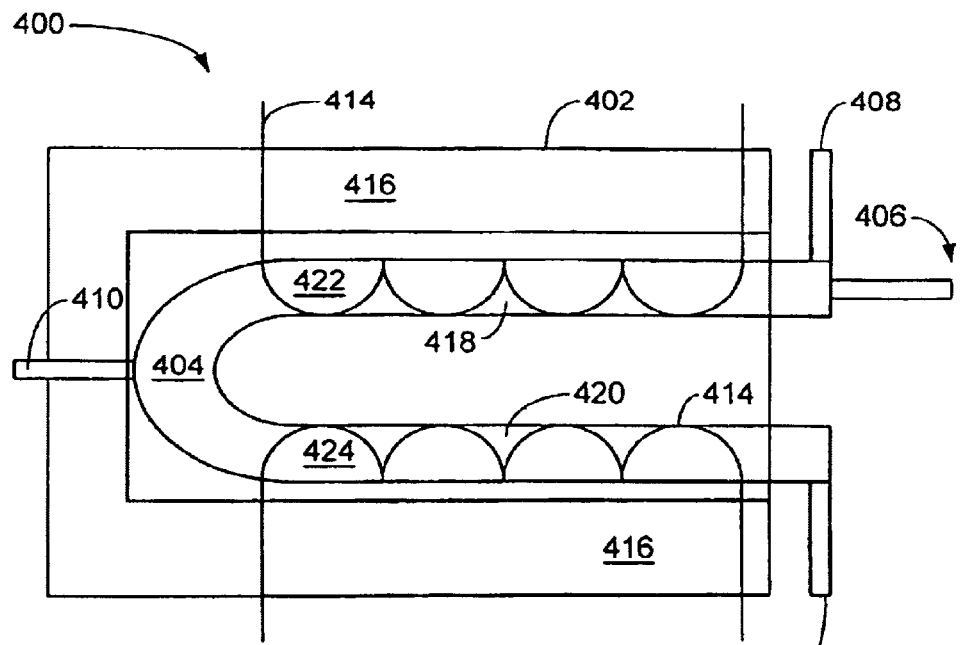
FIG. 4 is a cross-sectional view of an embodiment of a combustion device 400 of the present invention shown generally to include housing 402, combustion tube 404 having a sample inlet 406, a first oxidizing agent inlet 408, a second oxidizing agent inlet 410 downstream from the first inlet 408 and an outlet 412.

Referring now to FIG. 4, an embodiment of the combustion device generally as 400 of the present invention is shown to include a housing 402 enclosing a combustion tube 404 having a sample inlet 406, a first oxidizing agent inlet 408, a second oxidizing agent inlet 410 downstream from the first inlet 408 and an outlet 412. The device 400 also includes a heater 414 and preferably an insulator 416. The combustion tube 404 can either be a single tube as shown in the figure, or the tube 404 can comprise a first tube segment 418 and a second tube segment 420 with the second oxidizing agent inlet 410 interposed therebetween in the form of a T-connection. As the sample and the first amount of oxidizing agent enter the first segment 418 oxidation commences in a first oxidation zone 422. When the oxidizing mixture reaches the second oxidizing agent inlet 410, a second amount of oxidizing agent in injected into the mixture. This second amount of oxidizing agent improves oxidation efficiency in a second oxidizing zone 424 associated with the second tube segment 420.

Figure 5:
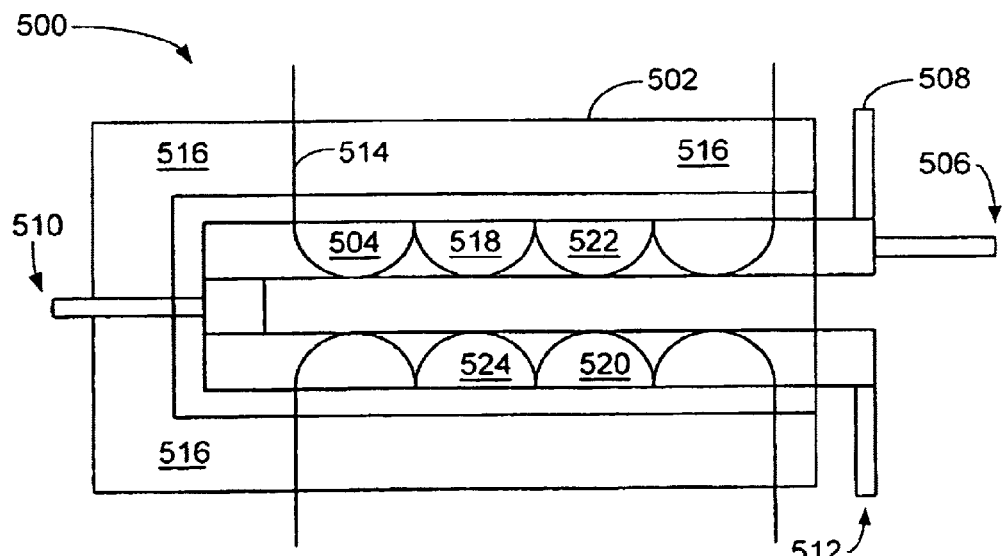
FIG. 5 is a cross-sectional view of an embodiment of a combustion device 500 of the present invention shown generally to include housing 502 enclosing a combustion tube 504 having a sample inlet 506, a first oxidizing agent inlet 508, a second oxidizing agent inlet 510 downstream from the first inlet 508 and an outlet 512.

Referring now to FIG. 5, an embodiment of the combustion device generally 500 of the present invention is shown to include a housing 502 enclosing a combustion tube 504 having a sample inlet 506, a first oxidizing agent inlet 508, a second oxidizing agent inlet 510 downstream from the first inlet 508 and an outlet 512. The device 500 also includes a heater 514 and preferably an insulator 516. The combustion tube 504 can either be a single tube or as shown in the figure, the tube 504 can comprise a first tube segment 518 and a second tube segment 520 with the second oxidizing agent inlet 510 interposed therebetween in the form of a T-connection. As the sample and the first amount of oxidizing agent enter the first segment 518 oxidation commences in a first oxidation zone 522. When the oxidizing mixture reaches the second oxidizing agent inlet 510, a second amount of oxidizing agent in injected into the mixture. This second amount of oxidizing agent improves oxidation efficiency in a second oxidizing zone 524 associated with the second tube segment 520.

Figure 6:
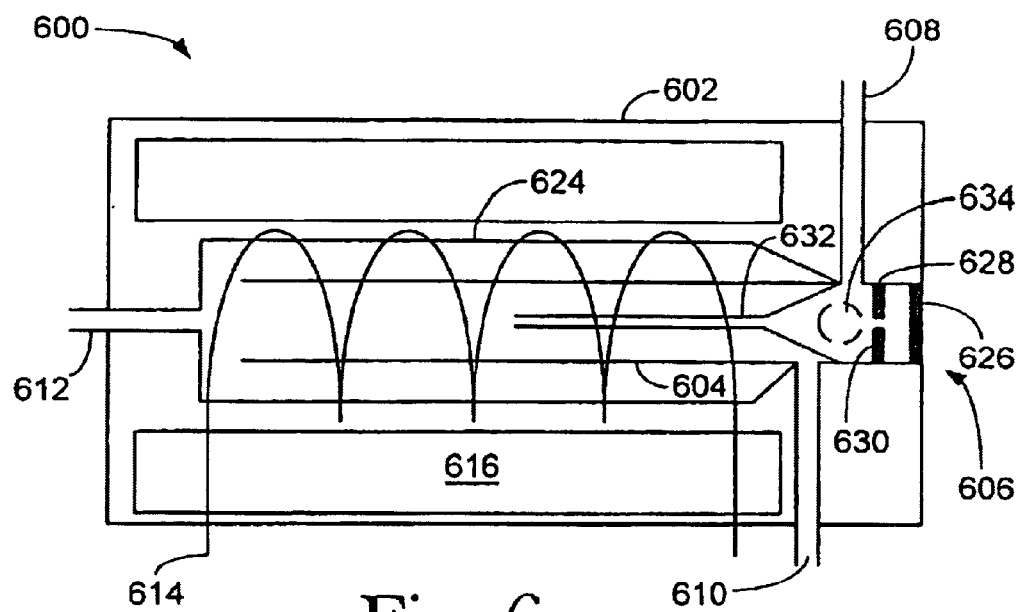
FIG. 6 is a cross-sectional view of an embodiment of a combustion device 600 of the present invention shown generally to include outer housing 602 enclosing an outer combustion tube 624, inner combustion tube 604, sample inlet 606 having septum 626, septum seat 628 defining passageway 630 and needle guide 632, inert gas inlet 608, a first oxidizing agent inlet 610, a second oxidizing agent inlet 612 and outlet 634.

Referring now to FIG. 6, an embodiment of the combustion device generally 600 of the present invention, designed to receive a direct injection of sample, is shown to include outer housing 602 enclosing an outer combustion tube 624, inner combustion tube 604, sample inlet 606 having septum 626, septum seat 628 defining passageway 630 and needle guide 632, inert gas inlet 608, a first oxidizing agent inlet 610, a second oxidizing agent inlet 612 and outlet 634. The device 600 may also includes heater 614 and insulator 616. As the sample is injected through septum 626, it is mixed with a first amount of oxidizing agent, introduced via first oxidation inlet 610. A first oxidation is commenced in inner combustion tube 604. As the oxidizing mixture proceeds through inner tube 604, a second amount of oxidizing agent, introduced via second oxidation inlet 612, is injected into the mixture. This second amount of oxidizing agent is introduced counter-flow to the oxidizing mixture exiting inner tube 604 to create turbulent flow mixing. While not wishing to be limited by theory, the inventor believes the mixing caused by the turbulent flow improves the oxidation efficiency of the sample. The resulting oxidized sample exits outlet 634. In a preferred embodiment of device 600, and to further increase turbulent flow for the oxidizing agents, either or both inner tube 604 and outer tube 624 maybe be packed with inert packing materials.

Figure 7:
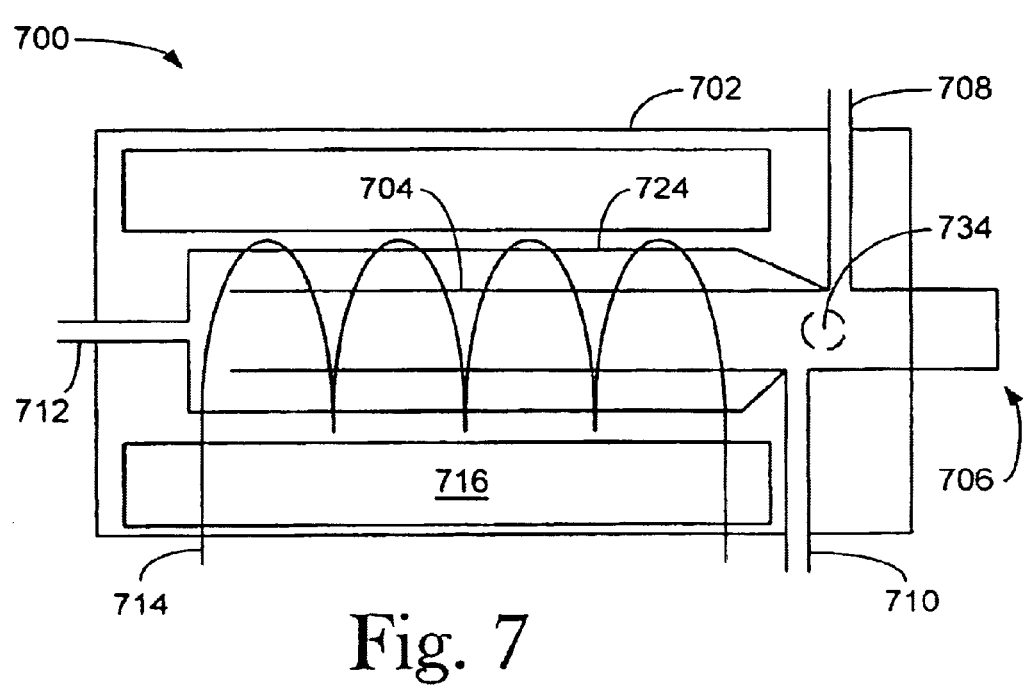
FIG. 7 is a cross-sectional view of an embodiment of a combustion device 700 of the present invention shown generally to include outer housing 702 enclosing an outer combustion tube 724, inner combustion tube 704, sample inlet 706, inert gas inlet 708, a first oxidizing agent inlet 710, a second oxidizing inlet 712 and outlet 734.

Referring now to FIG. 7, an embodiment of the combustion device generally 700 of the present invention, designed to receive a sample from a sample interface, an example of which could be a nebulizer, atomizer or the like, is shown to include outer housing 702 enclosing an outer combustion tube 724, inner combustion tube 704, sample inlet 706, inert gas inlet 708, a first oxidizing agent inlet 710, a second oxidizing inlet 712 and outlet 734. The device 700 may also includes heater 714 and insulator 716. As the sample is introduced through inlet 706, it is mixed with a first amount of oxidizing agent, introduced via first oxidation inlet 710. A first oxidation is commenced in inner combustion tube 704. As the oxidizing mixture proceeds through inner tube 704, a second amount of oxidizing agent, introduced via second oxidation inlet 712, is injected into the mixture. This second amount of oxidizing agent is introduced counter-flow to the oxidizing mixture exiting inner tube 704 to create turbulent flow mixing. While not wishing to be limited by theory, the inventor believes the mixing caused by the turbulent flow improves the oxidation efficiency of the sample. The resulting oxidized sample exits outlet 712. In a preferred embodiment of device 700, and to further increase turbulent flow for the oxidizing agents, either or both inner tube 704 and outer tube 724 maybe be packed with inert packing materials.

EXAMPLES

The following examples are included for the sake of completeness of disclosure and to illustrate the present invention, but in no way are these examples included for the sake of limiting the scope or teaching of this disclosure.

This example illustrates the improved detection limits and the improved relative percent standard deviation (% RSD) obtained from use of the device of the present invention over prior art devices. The calibration curve data obtained from analysis of sulfur standards by use of a prior art combustion device are shown in Table 1, and the calibration curve data obtained from analysis of sulfur standards by use of a multi-stage combustion tube of the present invention are shown in Table 2. For example, the data in Tables 1 and 2 illustrate that there is a significant increase in sulfur counts (Scnts), obtained for sulfur standards (concentration in ppb) when the device of the present invention is utilized. Of most significance in the increase in sulfur counts obtained for the 1000 ppb standard.

Figure 8:
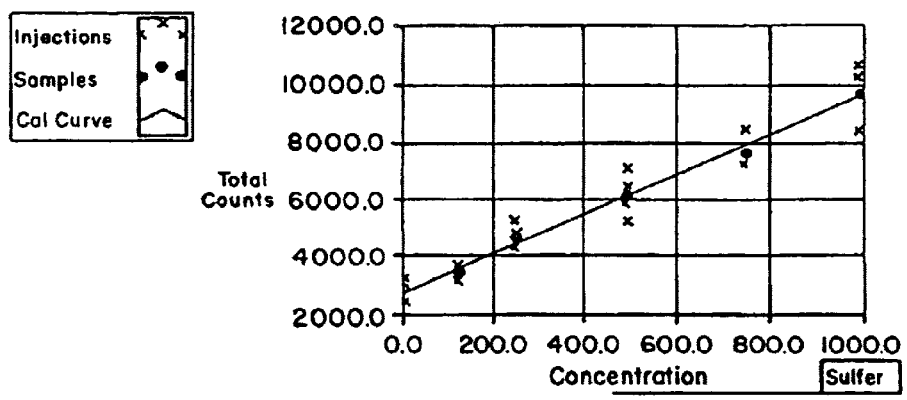
FIG. 8 is a calibration curve of counts v. concentration of sulfur obtained with use of a prior art combustion tube.
Figure 9:
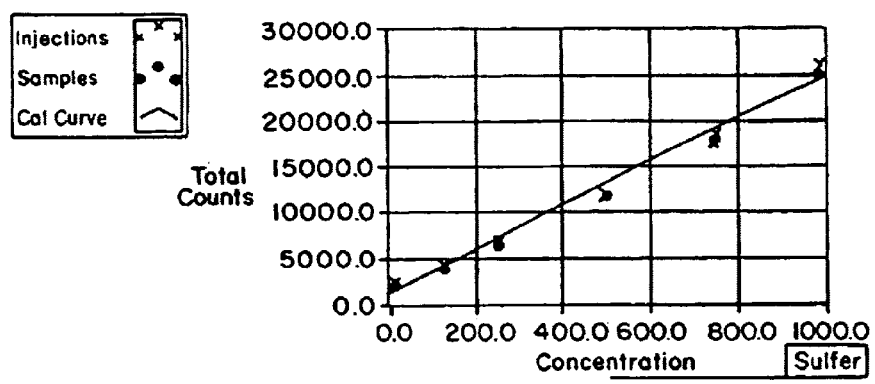
FIG. 9 is a calibration curve of counts v. concentration of sulfur obtained with use of the combustion tube of the present invention.

Referring now additionally to FIG. 8, which is a calibration curve of counts v. concentration of sulfur in ppb obtained with use of a prior art combustion tube (Table 1), and to FIG. 9, which is a calibration curve of counts v. concentration of sulfur in ppb obtained with use of the combustion tube of the present invention (Table 2), there is graphically demonstrated, by the relative scattering of the data points, that the reproducibility of the total counts obtained from use of the multi-stage combustion tube of the present invention is a marked improvement over the reproducibility of the total counts obtained from use of the prior art combustion tube.

TABLE 1

Sulfur Calibration Data utilizing prior art device

| Name | Use N | Use S | S Conc | S Cnts | S % RSDonis |
|---|---|---|---|---|---|
| Standard 1 | X | X | 0.00 | 2845.8 | 12.68 |
| Standard 1.1 | X | X | 0.00 | 3183.2 | |
| Standard 1.2 | X | X | 0.00 | 2568.9 | |
| Standard 1.3 | X | X | 0.00 | 2866.9 | |
| Standard 1.4 | X | X | 0.00 | 3199.4 | |
| Standard 1.5 | X | X | 0.00 | 2390.5 | |
| Standard 2 | X | X | 125.00 | 3384.1 | 6.60 |
| Standard 2.1 | X | X | 125.00 | 3050.2 | |
| Standard 2.2 | X | X | 125.00 | 3502.2 | |
| Standard 2.3 | X | X | 125.00 | 3633.6 | |
| Standard 2.4 | X | X | 125.00 | 3292.6 | |
| Standard 2.5 | X | X | 125.00 | 3441.5 | |
| Standard 3 | X | X | 250.00 | 4637.8 | 8.82 |
| Standard 3.1 | X | X | 250.00 | 4729.9 | |
| Standard 3.2 | X | X | 250.00 | 4160.8 | |
| Standard 3.3 | X | X | 250.00 | 4766.9 | |
| Standard 3.4 | X | X | 250.00 | 5196.6 | |
| Standard 3.5 | X | X | 250.00 | 4294.8 | |
| Standard 4 | X | X | 500.00 | 6113.6 | 11.16 |
| Standard 4.1 | X | X | 500.00 | 6407.9 | |
| Standard 4.2 | X | X | 500.00 | 5146.0 | |
| Standard 4.3 | X | X | 500.00 | 5916.8 | |
| Standard 4.4 | X | X | 500.00 | 7007.7 | |
| Standard 4.5 | X | X | 500.00 | 6089.6 | |
| Standard 5 | X | X | 750.00 | 7600.1 | 6.31 |
| Standard 5.1 | X | X | 750.00 | 7402.7 | |
| Standard 5.2 | X | X | 750.00 | 7626.2 | |
| Standard 5.3 | X | X | 750.00 | 8414.0 | |
| Standard 5.4 | X | X | 750.00 | 7209.1 | |
| Standard 5.5 | X | X | 750.00 | 7346.5 | |
| Standard 6 | X | X | 1000.00 | 9807.0 | 9.55 |
| Standard 6.1 | X | X | 1000.00 | 6302.1 | |
| Standard 6.2 | X | X | 1000.00 | 10413.5 | |
| Standard 6.3 | X | X | 1000.00 | 10217.4 | |
| Standard 6.4 | X | X | 1000.00 | 9509.7 | |
| Standard 6.5 | X | X | 1000.00 | 10592.5 | |

The calibration curve plotted from the data in Table 1 appears in FIG. 8.

TABLE 2

Sulfur Calibration Data utilizing staged oxidation chamber of the present invention

| Name | Use N | Use S | S Conc | S Cnts | S % RSDonis |
|---|---|---|---|---|---|
| Standard 1 | X | X | 0.00 | 2002.9 | 11.70 |
| Standard 1.1 | X | X | 0.00 | 1960.5 | |
| Standard 1.2 | X | X | 0.00 | 1884.2 | |
| Standard 1.3 | X | X | 0.00 | 2289.7 | |
| Standard 1.4 | X | X | 0.00 | 1695.9 | |
| Standard 1.5 | X | X | 0.00 | 2284.2 | |
| Standard 2 | X | X | 125.00 | 4008.6 | 6.30 |
| Standard 2.1 | X | X | 125.00 | 3747.7 | |
| Standard 2.2 | X | X | 125.00 | 4346.8 | |
| Standard 2.3 | X | X | 125.00 | 8771.2 | |
| Standard 2.4 | X | X | 125.00 | 4058.0 | |
| Standard 2.5 | X | X | 125.00 | 4128.8 | |
| Standard 3 | X | X | 250.00 | 6684.4 | 3.59 |
| Standard 3.1 | X | X | 250.00 | 6882.9 | |

TABLE 2-continued

Sulfur Calibration Data utilizing staged oxidation chamber of the present invention

| Name | Use N | Use S | S Conc | S Cnts | S % RSDonis |
|---|---|---|---|---|---|
| Standard 3.2 | X | X | 250.00 | 6604.9 | |
| Standard 3.3 | X | X | 250.00 | 6640.5 | |
| Standard 3.4 | X | X | 250.00 | 6556.4 | |
| Standard 3.5 | X | X | 250.00 | 6187.5 | |
| Standard 4 | X | X | 500.00 | 11647.3 | 2.16 |
| Standard 4.1 | X | X | 500.00 | 11473.3 | |
| Standard 4.2 | X | X | 500.00 | 11852.9 | |
| Standard 4.3 | X | X | 500.00 | 11644.3 | |
| Standard 4.4 | X | X | 500.00 | 11970.2 | |
| Standard 4.5 | X | X | 500.00 | 11896.0 | |
| Standard 5 | X | X | 750.00 | 17597.0 | 2.76 |
| Standard 5.1 | X | X | 750.00 | 17396.6 | |
| Standard 5.2 | X | X | 750.00 | 17485.0 | |
| Standard 5.3 | X | X | 750.00 | 17864.4 | |
| Standard 5.4 | X | X | 750.00 | 18458.7 | |
| Standard 5.5 | X | X | 750.00 | 17828.2 | |
| Standard 6 | X | X | 1000.00 | 25627.2 | 2.79 |
| Standard 6.1 | X | X | 1000.00 | 26178.2 | |
| Standard 6.2 | X | X | 1000.00 | 26225.5 | |
| Standard 6.3 | X | X | 1000.00 | 24448.6 | |
| Standard 6.4 | X | X | 1000.00 | 26678.5 | |
| Standard 6.5 | X | X | 1000.00 | 26812.4 | |

The calibration curve plotted from the data in Table 2 appears in FIG. 9.

Although the invention has been disclosed with reference to its preferred embodiments, from reading this description those of skill in the art may appreciate changes and modification that may be made which do not depart from the scope and spirit of the invention as described above and claimed hereafter.

What is claimed is:

1. A method for oxidizing samples comprising the steps of:
   introducing a sample and a first amount of an oxidizing agent into an oxidation chamber maintained at an elevated temperature, and
   introducing at least one additional amount of the oxidizing agent into the combustion chamber,
   where the combustion chamber comprises an inner tube having an interior and an exterior and an outer tube having an interior, where the first amount of oxidizing agent oxidizes the sample in a first combustion zone, which comprises the interior of the inner tube and the at least one additional amount of the oxidizing agent continues to oxidize the sample in a second combustion zone, which comprises a region between the exterior of the inner tube and the interior of the outer tube, where the first and additional amounts of the oxidizing agent are in excess of a stoichiometric amount of oxidizing agent needed to completely convert all oxidizable components in the sample into their corresponding oxides, where the oxidizable components are partially or completely convened into their corresponding oxides, and where the introduction the additional amounts of oxidizing agent improves an oxidation efficiency of the combustion chamber.

2. The method of claim 1, further comprising the step of:
   atomizing or nebulizing the sample and the first amount of the oxidizing agent prior to the first introducing step in an atomizer or nebulizer.

3. The method of claim 1, further comprising the steps of:
   atomizing or nebulizing the sample and the first amount of the oxidizing agent prior to the first introducing step in an atomizer or nebulizer;

forwarding the oxides to at least one species specific detector; and detecting at least one oxide of nitrogen, phosphorus and/or sulfur in the at least one species specific detector.

4. The method of claim 1, further comprising the steps of:

separating the sample into its components in a separation apparatus;

atomizing or nebulizing each sample component and the first amount of the oxidizing agent prior to the first introducing step in an atomizer or nebulizer;

forwarding the oxides to at least one species specific detector; and detecting at least one oxide of nitrogen, phosphorus and/or sulfur in the at least one species specific detector.

5. The method of claim 1, further comprising the steps of:

atomizing or nebulizing the sample and the first amount of the oxidizing agent prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

6. The method of claim 1, further comprising the steps of:

separating the sample into its components in a separation apparatus;

atomizing or nebulizing each sample component and the first amount of the oxidizing agent prior to the first introducing step in an atomizer or nebulizer;

transforming at least one oxide of sulfur to a sulfur species capable of undergoing ozone induced chemiluminescence after the second introducing step;

forwarding the oxides and the sulfur species to at least one species specific detector; and detecting at least one oxide of nitrogen, phosphorus and/or sulfur in the at least one species specific detector.

7. The method of claim 1, wherein the introduction of the first and at least one additional amounts of oxidizing agent improves liberation of nitrogen, phosphorus and/or sulfur from sample components containing nitrogen, phosphorus and/or sulfur and improves the detection of oxides of nitrogen, phosphorus and/or sulfur.

8. The method of claim 1, wherein a flow rate of the first amount of the oxidizing agent is between about 50 cc/min and about 1000 cc/min and a flow rate of the at least one additional amount of the oxidizing agent is between about 10 cc/min and about 300 cc/min.

9. The method of claim 1, wherein the elevated temperature is between about 300° and about 1600° C. and.

10. The method of claim 1, wherein the sample is introduced at a volume of from about 1 μL to 200 μL at a sample introduction rate of about 0.5 μL/sec to about 6 μL/sec.

11. A method for oxidizing samples comprising the steps of:

introducing a sample and a first amount of an oxidizing agent into an oxidation chamber maintained at an elevated temperature, and introducing at least one additional amount of the oxidizing agent into the combustion chamber, where the combustion chamber comprises a U-shaped combustion tube and where the at least one additional amount of the oxidizing agent is introduced into the U-shaped combustion tube at about a turn in the U-shaped combustion tube, where the first and additional amounts of the oxidizing a gent are in excess of a stoichiometric a mount of oxidizing agent needed to completely convert all oxidizable components in the sample into their corresponding oxides, where the oxidizable components are partially or completely converted into their corresponding oxides, and where the introduction of the first and additional amounts of oxidizing agent improves an oxidation efficiency of the combustion chamber.

12. The method of claim 11, further comprising the step of:

atomizing or nebulizing the sample and the first amount of the oxidizing agent prior to the first introducing step in an atomizer or nebulizer.

13. The method of claim 11, further comprising the steps of:

atomizing or nebulizing the sample and the first amount of the oxidizing agent prior to the first introducing step in an atomizer or nebulizer;

forwarding the oxides to at least one species specific detector; and detecting at least one oxide of nitrogen, phosphorus and/or sulfur in the at least one species specific detector.

14. The method of claim 11, further comprising the steps of:

separating the sample into its components in a separation apparatus;

atomizing or nebulizing each sample component and the first amount of the oxidizing agent prior to the first introducing step in an atomizer or nebulizer;

forwarding the oxides to at least one species specific detector; and detecting at least one oxide of nitrogen, phosphorus and/or sulfur in the at least one species specific detector.

15. The method of claim 11, further comprising the steps of:

atomizing or nebulizing the sample and the first amount of the oxidizing agent prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

16. The method of claim 11, further comprising the steps of:

separating the sample into its components in a separation apparatus;

atomizing or nebulizing each sample component and the first amount of the oxidizing agent prior to the first introducing step in an atomizer or nebulizer;

transforming at least one oxide of sulfur to a sulfur species capable of undergoing ozone induced chemiluminescence after the second introducing step;

forwarding the oxides and the sulfur species to at least one species specific detector; and detecting at least one oxide of nitrogen, phosphorus and/or sulfur in the at least one species specific detector.

17. The method of claim 11, wherein the introduction of the first and at least one additional amounts of oxidizing agent improves liberation of nitrogen, phosphorus and/or sulfur form sample components containing nitrogen, phosphorus and/or sulfur and improves the detection of oxides of nitrogen, phosphorus and/or sulfur.

18. The method of claim 11, wherein a flow rate of the first amount of the oxidizing agent is between about 50 cc/min and about 1000 cc/min and a flow rate of the at least one additional amount of the oxidizing agent is between about 10 cc/min and about 300 cc/min.

19. The method of claim 11, wherein the elevated temperature is between about 300° and about 1600° C.

20. The method of claim 11, wherein a sample is introduced at a volume of from about 1 µL to 200 µL at a sample introduction rate of about 0.5 µL/sec to about 6 µL/sec.

21. A method for oxidizing samples comprising:

mixing a sample with a first amount of an oxidizing agent to form an oxidizing mixture;

introducing the oxidizing mixture into a first combustion zone of a combustion chamber;

converting a portion of oxidizable components of the sample into their corresponding oxides;

introducing a second amount of the oxidizing agent into a second combustion zone of the combustion chamber;

partially or completely converting all oxidizable components of the sample into their corresponding oxides, where the combustion chamber comprises an inner tube having an interior and an exterior and an outer tube having an interior, where the first amount of oxidizing agent oxidizes the sample in a first combustion zone, which comprises the interior of the inner tube and the at least one additional amount of the oxidizing agent continues to oxidize the sample in a second combustion zone, which comprises a region between the exterior of the inner tube and the interior of the outer tube, where the first and additional amounts of the oxidizing agent are in excess of a stoichiometric amount of oxidizing agent needed to completely convert all oxidizable components in the sample into their corresponding oxides, where the oxidizable components are partially or completely converted into their corresponding oxides, and where the introduction of the first and additional amounts of oxidizing agent improves an oxidation efficiency of the combustion chamber.

22. The method of claim 21, further comprising the step of:

atomizing or nebulizing the oxidizing mixture prior to the first introducing step in an atomizer or nebulizer.

23. The method of claim 21, further comprising the steps of:

atomizing or nebulizing the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

24. The method of claim 21, further comprising the steps of:

separating the sample into its components in a separation apparatus;

mixing and atomizing or nebulizing each sample component and the first amount of the oxidizing agent to form the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

25. The method of claim 21, further comprising the steps of:

atomizing or nebulizing the oxidizing mixture prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

26. The method of claim 21, further comprising the steps of:

separating the sample into its components in a separation apparatus;

mixing and atomizing or nebulizing each sample component and the first amount of the oxidizing agent to from the oxidizing mixture prior to the first introducing step in an atomizer or nebulizer;

transforming at least one oxide of sulfur to a sulfur species capable of undergoing ozone induced chemiluminescence after the second introducing step;

forwarding the oxides and the sulfur species to at least one species specific detector; and detecting at least one oxide of nitrogen, phosphorus and/or sulfur in the at least one species specific detector.

27. The method of claim 21, wherein the introduction of the first and at least one additional amounts of oxidizing agent improves liberation of nitrogen, phosphorus and/or sulfur form sample components containing nitrogen, phosphorus and/or sulfur and improves the detection of oxides of nitrogen, phosphorus and/or sulfur.

28. The method of claim 21, wherein a flow rate of the first amount of the oxidizing agent is between about 50 cc/min and about 1000 cc/min and a flow rate of the at least one additional amount of the oxidizing agent is between about 10 cc/min and about 300 cc/min.

29. The method of claim 21, wherein the elevated temperature is between about 300° and about 1600° C.

30. The method of claim 21, wherein a sample is introduced at a volume of from about 1 µL to 200 µL at a sample introduction rate of about 0.5 µL/sec to about 6 µL/sec.

31. A method for oxidizing samples comprising:

mixing a sample with a first amount of an oxidizing agent to form an oxidizing mixture;

introducing the oxidizing mixture into a first combustion zone of a combustion chamber;

converting a portion of oxidizable components of the sample into their corresponding oxides;

introducing a second amount of the oxidizing agent into a second combustion zone of the combustion chamber;

partially or completely converting all oxidizable components of the sample into their corresponding oxides, where the combustion chamber comprises a U-shaped combustion tube and where the at least one additional amount of the oxidizing agent is introduced into the U-shaped combustion tube at about a turn in the U-shaped combustion tube, where the first and additional a mounts of the oxidizing agent are in excess of a stoichiometric a mount of oxidizing agent needed to completely convert all oxidizable components in the sample into their corresponding oxides, the oxidizable components are partially or completely converted into their corresponding oxides, and where the introduction of the first and additional amounts of oxidizing agent improves an oxidation efficiency of the combustion chamber.

32. The method of claim 31, further comprising the step of:

atomizing or nebulizing the oxidizing mixture prior to the first introducing step in an atomizer or nebulizer.

33. The method of claim 31, further comprising the steps of:

atomizing or nebulizing the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

34. The method of claim 31, further comprising the steps of:

separating the sample into its components in a separation apparatus;

mixing and atomizing or nebulizing each sample component and the first amount of the oxidizing agent to form the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

35. The method of claim 31, further comprising the steps of:

atomizing or nebulizing the oxidizing mixture prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

36. The method of claim 31, further comprising the steps of:

separating the sample into its components in a separation apparatus;

mixing and atomizing or nebulizing each sample component and the first amount of the oxidizing agent to from the oxidizing mixture prior to the first introducing step in an atomizer or nebulizer;

transforming at least one oxide of sulfur to a sulfur species capable of undergoing ozone induced chemiluminescence after the second introducing step;

forwarding the oxides and the sulfur species to at least one species specific detector; and detecting at least one oxide of nitrogen, phosphorus and/or sulfur in the at least one species specific detector.

37. The method of claim 31, wherein the introduction of the first and at least one additional amounts of oxidizing agent improves liberation of nitrogen, phosphorus and/or sulfur form sample components containing nitrogen, phosphorus and/or sulfur and improves the detection of oxides of nitrogen, phosphorus and/or sulfur.

38. The method of claim 31, wherein a flow rate of the first amount of the oxidizing agent is between about 50 cc/min and about 1000 cc/min and a flow rate of the at least one additional amount of the oxidizing agent is between about 10 cc/min and about 300 cc/min.

39. The method of claim 31, wherein the elevated temperature is between about 300° and about 1600° C.

40. The method of claim 31, wherein a sample is introduced at a volume of from about 1 µL to 200 µL at a sample introduction rate of about 0.5 µL/sec to about 6 µL/sec.

41. A method for oxidizing samples comprising:

separating a sample into its components in a separation apparatus;

mixing each component with a first amount of an oxidizing agent;

introducing each component and a first amount of the oxidizing agent into a combustion chamber maintained at an elevated temperature;

converting a portion of oxidizable components of the sample into their corresponding oxides;

introducing at least one additional amount of the oxidizing agent; and partially or completely converting each component of the sample into its corresponding oxides, where the combustion chamber comprises an inner tube having an interior and an exterior and an outer tube having an interior, where the first amount of oxidizing agent oxidizes the sample in a first combustion zone, which comprises the interior of the inner tube and the at least one additional amount of the oxidizing agent continues to oxidize the sample in a second combustion zone, which comprises a region between the exterior of the inner tube and the interior of the outer tube, where the first and additional amounts of the oxidizing agent are in excess of a stoichiometric amount of oxidizing agent needed to completely convert all oxidizable components in the sample into their corresponding oxides, where the oxidizable components are partially or completely converted into their corresponding oxides, and where the introduction of the first and additional amounts of oxidizing agent improves an oxidation efficiency of the combustion chamber.

42. The method of claim 41, further comprising the step of:

atomizing or nebulizing the oxidizing mixture prior to the first introducing step in an atomizer or nebulizer.

43. The method of claim 41, further comprising the steps of:

atomizing or nebulizing the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

44. The method of claim 41, further comprising the steps of:

atomizing or nebulizing the oxidizing mixture prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

45. The method of claim 41, wherein the introduction of the first and at least one additional amounts of oxidizing agent improves liberation of nitrogen, phosphorus and/or sulfur form sample components containing nitrogen, phosphorus and/or sulfur and improves the detection of oxides of nitrogen, phosphorus and/or sulfur.

46. The method of claim 41, wherein a flow rate of the first amount of the oxidizing agent is between about 50 cc/min and about 1000 cc/min and a flow rate of the at least one additional amount of the oxidizing agent is between about 10 cc/min and about 300 cc/min.

47. The method of claim 41, wherein the elevated temperature is between about 300° and about 1600° C.

48. The method of claim 41, wherein a sample is introduced at a volume of from about 1 μL to 200 μL at a sample introduction rate of about 0.5 μL/sec to about 6 μL/sec.

49. A method for oxidizing samples comprising:

separating a sample into its components in a separation apparatus;

mixing each component with a first amount of an oxidizing agent;

introducing each component and a first amount of the oxidizing agent into a combustion chamber maintained at an elevated temperature;

converting a portion of oxidizable components of the sample into their corresponding oxides;

introducing at least one additional amount of the oxidizing agent; and partially or completely converting each component of the sample into its corresponding oxides, where the combustion chamber comprises a U-shaped combustion tube and where the at least one additional amount of the oxidizing agent is introduced into the U-shaped combustion tube at about a turn in the U-shaped combustion tube, where the first and additional a mounts of the oxidizing agent are in excess of a stoichiometric a mount of oxidizing agent needed to completely convert all oxidizable components in the sample into their corresponding oxides, where the oxidizable components are partially or completely converted into their corresponding oxides, and where the introduction of the first and additional amounts of oxidizing agent improves an oxidation efficiency of the combustion chamber.

50. The method of claim 49, further comprising the step of:

atomizing or nebulizing the oxidizing mixture prior to the first introducing step in an atomizer or nebulizer.

51. The method of claim 49, further comprising the steps of:

atomizing or nebulizing the oxidizing mixture prior to the first introducing step in an atomizer or nebulizer;

forwarding the oxides to at least one species specific detector; and detecting at least one oxide of nitrogen, phosphorus and/or sulfur in the at least one species specific detector.

52. The method of claim 49, further comprising the steps of:

atomizing or nebulizing the oxidizing mixture prior to the first introducing step in an atomizer or nebulizer;

transforming at least one oxide of sulfur to a sulfur species capable of undergoing ozone induced chemiluminescence;

forwarding the oxides and the sulfur species to at least one species specific detector; and detecting at least one oxide of nitrogen, phosphorus and/or sulfur in the at least one species specific detector.

53. The method of claim 49, wherein the introduction of the first and at least one additional amounts of oxidizing agent improves liberation of nitrogen, phosphorus and/or sulfur form sample components containing nitrogen, phosphorus and/or sulfur and improves the detection of oxides of nitrogen, phosphorus and/or sulfur.

54. The method of claim 49, wherein a flow rate of the first amount of the oxidizing agent is between about 50 cc/min and about 1000 cc/min and a flow rate of the at least one additional amount of the oxidizing agent is between about 10 cc/min and about 300 cc/min.

55. The method of claim 49, wherein the elevated temperature is between about 300° and about 1600° C.

56. The method of claim 49, wherein a sample is introduced at a volume of from about 1 μL to 200 μL at a sample introduction rate of about 0.5 μL/sec to about 6 μL/sec.

* * * * *